US007575588B2

(12) United States Patent
Barker et al.

(10) Patent No.: US 7,575,588 B2
(45) Date of Patent: Aug. 18, 2009

(54) MIDLINE OCCIPITAL VERTEBRAL FIXATION SYSTEM (75) Inventors: B. Thomas Barker, Bartlett, TN (US); Eric Steven Heinz, Memphis, TN (US); Ian Farey, Chatswood (AU)

(73) Assignee: Warsaw Orthopedic Inc., Warsaw, IN (US)

( * ) Notice: Subject to any disclaimer, the term of this patent is extended or adjusted under 35 U.S.C. 154(b) by 264 days.

(21) Appl. No.: 10/704,767

(22) Filed: Nov. 10, 2003

(65) Prior Publication Data
US 2004/0153070 A1 Aug. 5, 2004

Related U.S. Application Data (60) Provisional application No. 60/444,485, filed on Feb. 3, 2003, provisional application No. 60/486,145, filed on Jul. 10, 2003.

(51) Int. Cl.
*A61B 17/80* (2006.01)
(52) U.S. Cl. .............................. 606/280; 606/70; 606/60
(58) Field of Classification Search .................. 606/61, 606/69–71, 60, 246, 250–251, 279, 280–299, 606/902–903, 905–906
See application file for complete search history.

(56) References Cited

U.S. PATENT DOCUMENTS

| 4,003,376 | A |   | 1/1977  | McKay et al. |
|-----------|---|---|---------|--------------|
| 4,773,402 | A |   | 9/1988  | Asher et al. |
| 4,887,595 | A |   | 12/1989 | Heinig et al. |
| 4,998,936 | A |   | 3/1991  | Mehdian |
| 5,030,220 | A | * | 7/1991  | Howland ...................... 606/61 |
| 5,127,912 | A |   | 7/1992  | Ray et al. |
| 5,133,717 | A | * | 7/1992  | Chopin ........................ 606/61 |
| 5,147,360 | A |   | 9/1992  | Dubousset |
| 5,330,473 | A | * | 7/1994  | Howland ...................... 606/61 |
| 5,360,429 | A |   | 11/1994 | Jeanson et al. |
| 5,366,455 | A | * | 11/1994 | Dove et al. .................... 606/61 |
| 5,476,463 | A |   | 12/1995 | Boachie-Adjei et al. |
| 5,545,164 | A | * | 8/1996  | Howland ...................... 606/61 |
| 5,582,612 | A | * | 12/1996 | Lin ............................. 606/61 |
| 5,593,407 | A |   | 1/1997  | Reis |
| 5,616,144 | A | * | 4/1997  | Yapp et al. .................... 606/61 |
| 5,681,312 | A |   | 10/1997 | Yuan et al. |
| 5,713,900 | A |   | 2/1998  | Benzel et al. |
| 5,755,798 | A | * | 5/1998  | Papavero et al. ......... 623/17.16 |
| 5,800,433 | A |   | 9/1998  | Benzel et al. |
| 5,814,046 | A | * | 9/1998  | Hopf ........................... 606/61 |
| 5,843,082 | A |   | 12/1998 | Yuan et al. |

(Continued)

FOREIGN PATENT DOCUMENTS

WO  WO 97/23170  7/1997

(Continued)

*Primary Examiner*—Thomas C Barrett
*Assistant Examiner*—James L Swiger (57) ABSTRACT An occipital plating system includes a plate extending along a longitudinal axis. The plate is engageable to the occiput, and includes at least one coupling member laterally offset relative to the longitudinal axis of the plate. The coupling member extends along a portion of the length of the plate. The at least one coupling member includes a passage to receive a connecting element. The coupling member is structured to at least medially and laterally constrain a portion of a length of the connecting element positioned in the passage.

17 Claims, 9 Drawing Sheets

U.S. PATENT DOCUMENTS

| | | |
|---|---|---|
| 5,928,232 A | 7/1999 | Howland et al. |
| 5,928,233 A | 7/1999 | Apfelbaum et al. |
| 6,036,693 A * | 3/2000 | Yuan et al. .................. 606/61 |
| 6,117,135 A | 9/2000 | Schlapfer |
| 6,146,382 A | 11/2000 | Hurlbert |
| 6,193,720 B1 | 2/2001 | Yuan et al. |
| 6,214,005 B1 | 4/2001 | Benzel et al. |
| 6,290,703 B1 | 9/2001 | Ganem |
| 6,475,219 B1 | 11/2002 | Shelokov |
| 6,524,315 B1 * | 2/2003 | Selvitelli et al. ............ 606/70 |
| 6,547,790 B2 * | 4/2003 | Harkey et al. ................. 606/61 |
| 2002/0042614 A1 | 4/2002 | Ueyama et al. |
| 2002/0049446 A1 | 4/2002 | Harkey, III et al. |
| 2002/0120268 A1 | 8/2002 | Berger |
| 2003/0153913 A1 * | 8/2003 | Altarac et al. ................. 606/61 |
| 2004/0162558 A1 * | 8/2004 | Hegde et al. .................. 606/61 |
| 2005/0228386 A1 * | 10/2005 | Ziolo et al. ................... 606/69 |

FOREIGN PATENT DOCUMENTS

WO     WO 01/97744 A2     12/2001

* cited by examiner

MIDLINE OCCIPITAL VERTEBRAL FIXATION SYSTEM

CROSS-REFERENCE TO RELATED APPLICATIONS

The present application claims the benefit of the filing date of Provisional Application No. 60/444,485 filed on Feb. 3, 2003, and also claims the benefit of the filing date of Provisional Application No. 60/486,145 filed on Jul. 10, 2003.

BACKGROUND

To provide fixation of the cervical region of the spine, bone grafts have been employed for occipito-cervical fusion. Sub-occipital and sub-laminar wiring techniques, lateral occipital plates, and a "keyhole" technique have been employed to stabilize the cervical region during fusion. Wiring techniques have been found to not provide the desired rigid fixation and can result in complications with intradural penetration. Lateral plates lie very close to the surface of the skin and can require bi-cortical placement of screws. Keyhole techniques involve the creation of a burr hole and a keyway in the occiput. As a result, the complexity of the surgery is increased.

Systems for occipital cervical fixation are needed that provide adequate fixation and reduce the complexity of the surgery for implantation. The present invention is directed to satisfying these needs, among others.

SUMMARY

According to one aspect, an occipital plating system includes a plate extending along a longitudinal axis with a profile adapted for positioning along the medial nuchal line of the occiput. At least one coupling member extends from the plate and is laterally positioned relative to the longitudinal axis of the plate. The at least one coupling member forms a passage extending along a portion of the length of the plate. The coupling member is structured to at least medially and laterally constrain a portion of a length of a connecting element positioned in the passage.

According to another aspect, an occipital plating system includes a plate extending along a longitudinal axis that has a bottom surface profile adapted for positioning along the medial nuchal line of the occiput and an opposite top surface. The plate includes at least one coupling member extending from the plate and laterally positioned relative to the longitudinal axis of the plate. The at least one coupling member forms a passage extending along a portion of the length of the plate to receive a cephalad end of an elongated connecting element in the passage. The passage opens along a top surface of the connecting element. The coupling member further includes at least one receptacle opening at a top surface of the coupling member in communication with the passage. A fastener is engageable in the receptacle in contact with the cephalad end of the connecting element to secure the cephalad end of the connecting element between the fastener and the coupling member.

According to a further aspect, an occipital plating system includes a plate extending along a longitudinal axis with a profile adapted for positioning along the medial nuchal line of the occiput. The plate includes at least one coupling member extending from the plate that is laterally positioned relative to the longitudinal axis of the plate. The at least one coupling member forms a passage extending along a portion of the length of the plate. The coupling member is structured to radially constrain a cephalad end of the connecting element in the passage while simultaneously permitting axial adjustment of the connecting element in the passage.

According to a further aspect, an occipital plating system includes a plate extending along a longitudinal axis. The plate is structured for positioning along the medial nuchal line of the occiput. First and second coupling members extend along a respective one of opposite sides of the plate. The coupling members each include a passage to receive a cephalad end portion of an elongated connecting element therein. The plate includes a rectangular shape extending cephaladly from the first and second coupling members.

In a further aspect, a method for stabilizing the spine comprises: engaging a plate along a medial-nuchal line of the occiput; positioning an elongated connecting element along a first side of the spine; positioning a cephalad end of the connecting element in a passage of the plate, the passage being offset from the medial nuchal line to the first side of the spine; medially and laterally constraining the connecting element in the passage while simultaneously permitting axial adjustment of the position of the connecting element in the passage; and axially securing the connecting element in the passage.

These and other aspects will also be apparent from the following description.

DESCRIPTION OF THE ILLUSTRATED EMBODIMENTS

For the purpose of promoting an understanding of the principles of the invention, reference will now be made to the illustrated embodiments thereof and specific language will be used to describe the same. It will nevertheless be understood that no limitation of the scope of the invention is thereby intended. Any such alterations and further modifications in the invention, and any such further applications of the principles of the invention as described herein are contemplated as would normally occur to one skilled in the art to which the invention relates.

Figure 1:
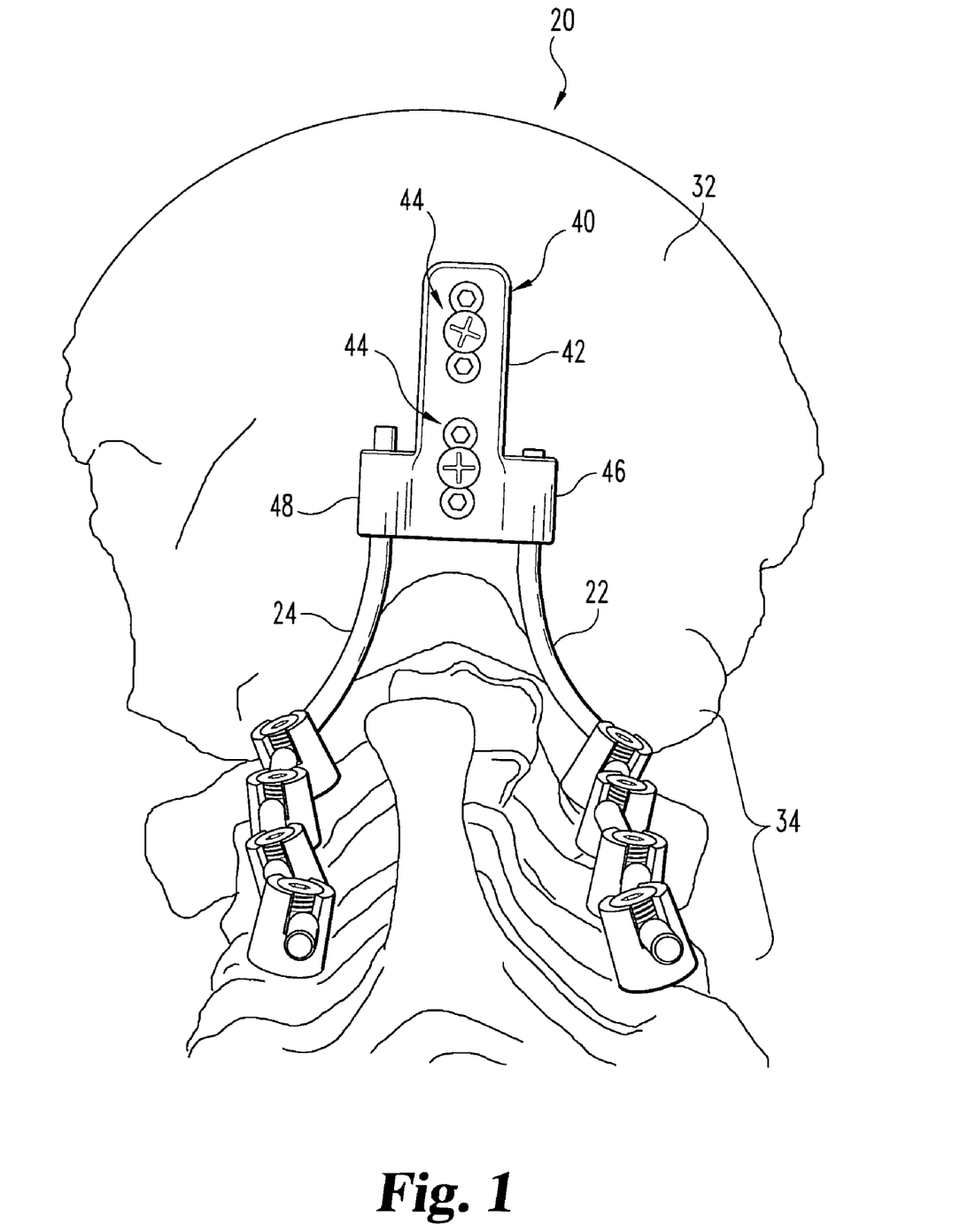
FIG. 1 shows a midline occipital vertebral fixation system looking cephaladly.
Figure 2:
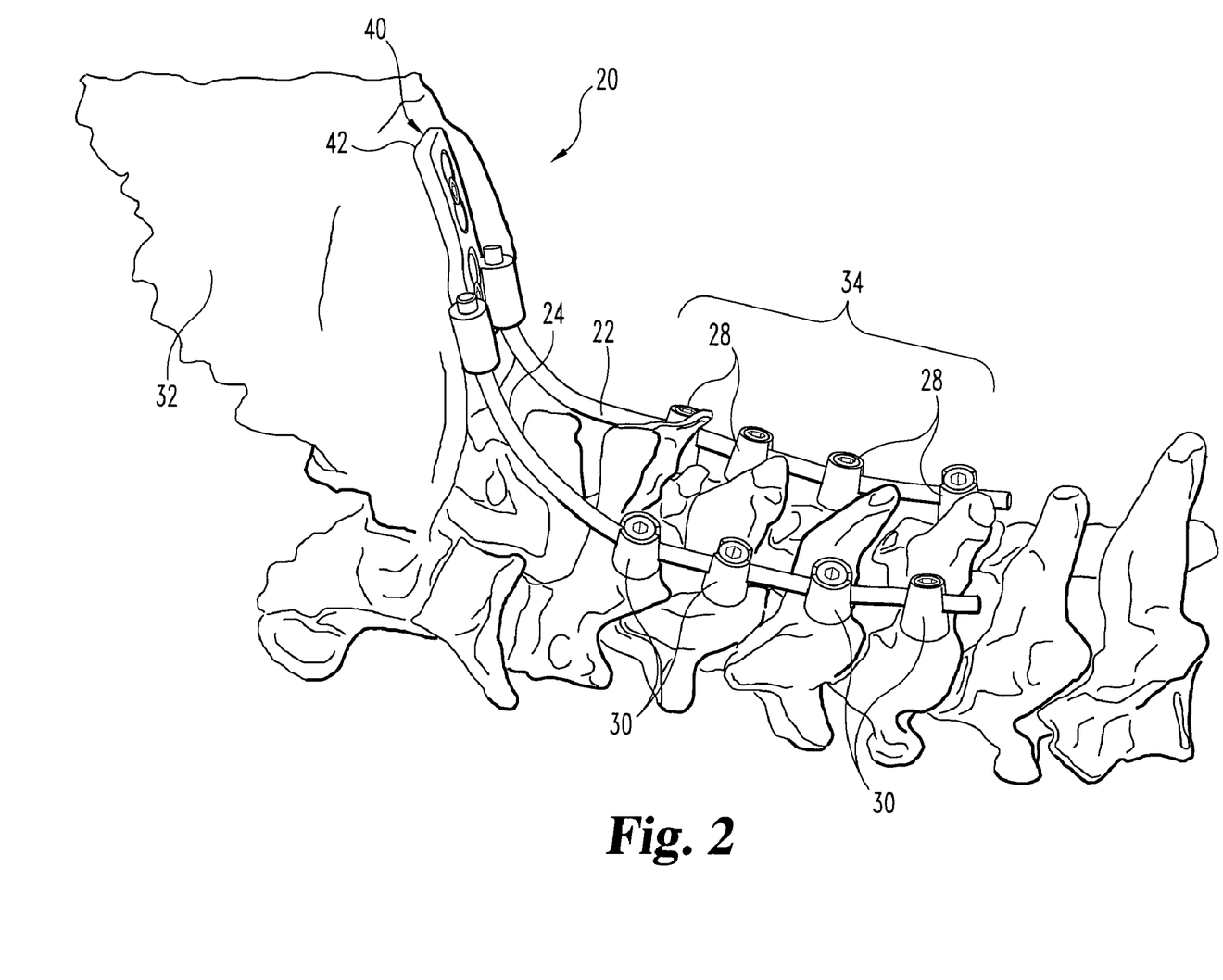
FIG. 2 shows the midline occipital vertebral fixation system of FIG. 1 looking laterally.

Referring to FIGS. 1 and 2, there is shown an occipital vertebral fixation system 20 including a plating system 40 and a vertebral fixation system 34. Plating system 40 includes a plate 42 engaged to occiput 32 and coupled with vertebral fixation system 34. Vertebral fixation system 34 is engaged to one or more of the cervical vertebrae. In the illustrated embodiment, vertebral fixation system 34 includes a first connecting element 22 and a second connecting element 24. Connecting elements 22, 24 are positioned along opposite sides of the spinous processes of the cervical vertebrae and engaged to posterior spinal elements thereof with anchors 28, 30, respectively.

Plating system 40 is positioned along the medial nuchal line of occiput 32. Plate 42 is engaged to the occiput with one or more fastening systems 44. Fastening systems 44 can include a single bone fastener, multiple bone fasteners, and one or more bone fasteners and retaining elements to prevent fastener backout. Connecting elements 22, 24 extend cephaladly from the cervical vertebrae and are coupled to coupling members 46, 48 of plate 42. Coupling members 46, 48 are laterally offset to opposite sides of the medial nuchal line to facilitate coupling with respective connecting elements 22, 24. Connecting elements 22, 24 can be bent, flexed or otherwise manipulated before or during surgery for coupling with plate 42 and to provide the desired fit with the patient's anatomy.

Figure 3:
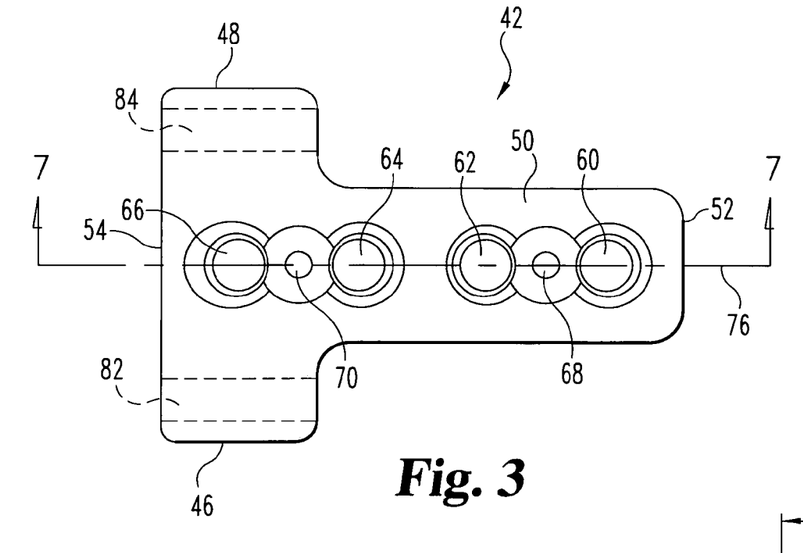
FIG. 3 is a plan view of a plate comprising a portion of the system of FIG. 1.
Figure 4:
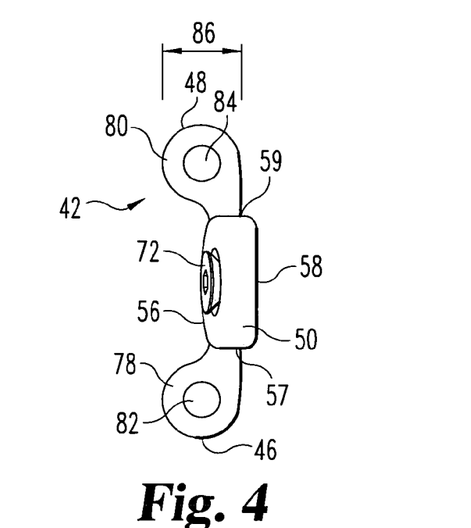
FIG. 4 is an end view of the plate of FIG. 3.
Figure 5:
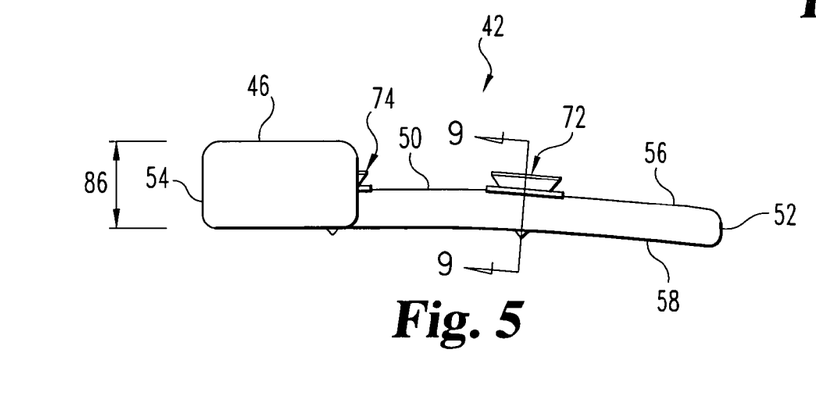
FIG. 5 is an elevation view of the plate of FIG. 3.
Figure 7:
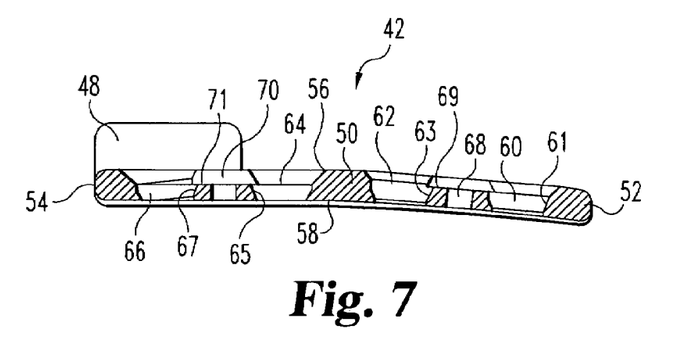
FIG. 7 is a section view through line 7-7 of FIG. 3.

Referring now to FIGS. 3-5, plate 42 includes a central body portion 50 extending between an upper or cephalad end 52 and a lower or caudal end 54. Body portion 50 includes a rectangular shape extending cephaladly from coupling members 46, 48. Plate 42 includes a top surface 56, a bottom surface 58 and sidewalls 57, 59 extending therebetween. When implanted, bottom surface 58 is positioned along the occiput and top surface 56 is oriented away from the occiput. As shown in FIGS. 5 and 7, plate 42 can include bottom surface 58 that is concavely curved along longitudinal axis 76 to conform to the profile of the occiput along the medial nuchal line when positioned thereon.

Figure 6:
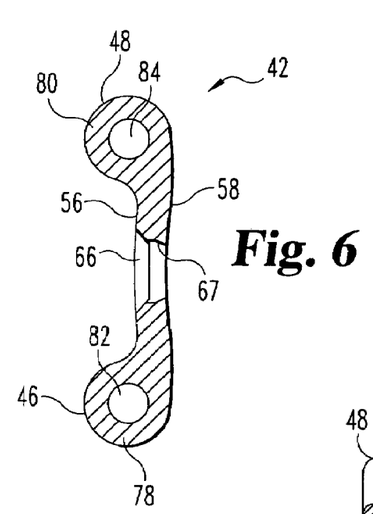
FIG. 6 is a section view through line 6-6 of FIG. 3.

As further shown in FIGS. 6-7, plate 42 includes a first set of bores 60, 62 that extend between and open at top surface 56 and bottom surface 58 for receiving a first set of bone engaging fasteners therethrough. Similarly, a second set of bores 64, 66 are provided that extend between and open at top surface 56 and bottom surface 58 for receiving a second set of bone engaging fasteners therethrough. First bore 60 includes a fastener bearing surface 61 having a spherical shape that contacts a correspondingly shaped spherical surface of the head of the bone engaging fastener positioned in bore 60. The complementary-shaped spherical surface allows the bone engaging fastener to assume any one of a plurality of angles relative to plate 42 about the center axis of bore 60. Second bore 62 includes a fastener bearing surface 63 adjacent to top surface 56 that is similar to fastener bearing surface 61. Bores 64, 66 can also be provided with fastener bearing surfaces 65, 67 similar to fastener bearing surfaces 61, 63.

It is contemplated that bores 60, 62, 64, 66 and the bone engaging fasteners therein can be configured so that the heads of the fasteners are recessed below top surface 56 when positioned in contact with bearing surfaces 61, 63, 65, 67. This configuration minimizes the profile of plating system 40 extending from the occiput and intrusion of the bone engaging fasteners into the adjacent tissue. Other embodiments contemplate that plate 42 is provided with less than four bone engaging fastener bores or more than four bone engaging fastener bores. The bone engaging fasteners and bores can also be adapted to provide a fixed orientation between the plate and the bone engaging fastener. Combination of fixed and variable angle placement of the bone engaging fasteners for the same plate are also contemplated. In the illustrated embodiment, bores 60, 62, 64, 66 are aligned along longitudinal axis 76 so that the width of plate 42 transversely to longitudinal axis 76 can be minimized. It is further contemplated that one or more of the bone engaging fastener bores can be offset to one side or the other of longitudinal axis 76, and also that bores can be positioned side-by-side on opposite sides of axis 76 to provide bi-lateral fixation.

Figure 8:
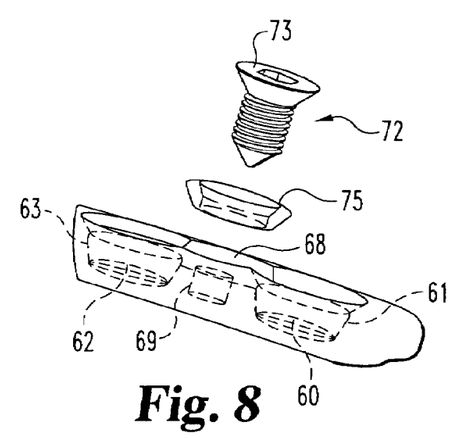
FIG. 8 is a perspective view of an end of the plate of FIG. 3 and one embodiment retaining system.
Figure 9:
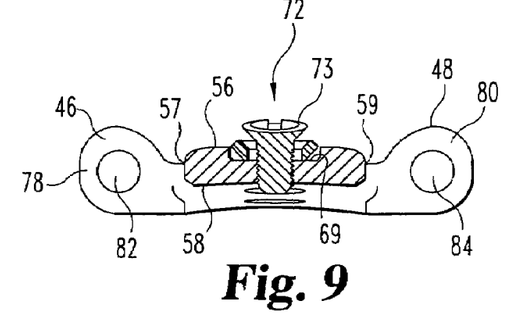
FIG. 9 is a section view through line 9-9 of FIG. 5.

As further shown in FIGS. 8-9, a retaining system receptacle 68 is formed between and in communication with bores 60, 62. A first retaining system 72 can be positioned in receptacle 68 to prevent back-out of bone engaging fasteners positioned in first and second bores 60, 62. A second retaining system receptacle 70 is formed between and in communication with bores 64, 66. A second retaining system 74 can be positioned in receptacle 70 to prevent back-out of bone engaging fasteners positioned in third and fourth bores 64, 66.

Receptacle 68 includes a flared upper portion 69 in communication with bores 60, 62 so that retaining system 72 can contact or be positioned adjacent the heads of the bone engaging fasteners in bores 60, 62. Receptacle 70 includes a flared upper portion 71 in communication with bores 64, 66 so that retaining system 74 can contact or be positioned adjacent the heads of the bone engaging fasteners in bores 64, 66. In the illustrated embodiment, retaining system 72 includes a retaining fastener 73 and a retaining element 75 secured to plate 42 with retaining fastener 73. When secured to plate 42, retaining element 75 is received in upper portion 69, and retaining fastener 73 extends through retaining element 75 and engages receptacle 68. The distal end of retaining fastener 73 can penetrate into the bone of the occiput, or can terminate in receptacle 68.

Other forms for retaining systems 72, 74 are also contemplated. For example, retaining fastener 73 may only extend partially into plate 42 for engagement therewith. Retaining fastener 73 and/or retaining element 75 can be threadingly engaged, riveted, and/or captured to plate 42. Retaining element 73 can be integral with retaining fastener 75. Retaining systems 72, 74 can be captured in or secured to plate 42 and rotated and/or longitudinally moved between a first position that permits insertion of bone engaging fasteners in the plate bores, and a second position that overlaps or contacts the bone engaging fasteners in the plate bores to prevent fastener backout. Retaining systems 72, 74 can be integral with plate 42 and movable between a fastener insertion position and a fastener retaining position. A retaining system can be provided for each bone engaging fastener, or a single retaining system can be provided for all bone engaging fasteners. Other suitable retaining systems are contemplated, including lock washers, caps and devices that expand the heads of the bone engaging fasteners. It is further contemplated that plating system 40 can be provided without any retaining systems.

Referring to FIGS. 3-9, plate 42 has a length extending along central longitudinal axis 76. First coupling member 46 extends laterally from body portion 50 along one side of axis 76, and second coupling member 48 extends laterally from body portion 50 along the opposite side of axis 76. Coupling members 46, 48 can be elongated and extend generally parallel to axis 76 along at least a portion of the length of body portion 50. In the illustrated embodiment, coupling members 46, 48 extend from lower end 54 toward upper end 52 in the direction of longitudinal axis 76. In one embodiment, it is contemplated that the length of coupling members 46, 48 is about 5 percent or more of the length of plate 42. In another embodiment, the length of coupling members 46, 48 ranges from about 5 percent to about 50 percent of the length of plate 42. In a further embodiment, it is contemplated that the length of coupling members 46, 48 ranges from about 15 percent to about 35 percent of the length of plate 42. In yet another embodiment, the length of coupling members 46, 48 is about 25 percent of the length of plate 42.

As shown in FIG. 4, coupling members 46, 48 are offset laterally from and project from the adjacent one of the lateral sidewalls 57, 59 of body portion 50. Coupling members 46, 48 include walls 78, 80 forming passages 82, 84, respectively. Passages 82, 84 extend at least partially through coupling members 46, 48 and in a direction parallel to longitudinal axis 76, although non-parallel orientations are also contemplated. Coupling members 46, 48 further each include a height 86 such that each of the coupling members 46, 48 extends above top surface 56 of body portion 50, as shown in FIGS. 4 and 5. The bottom surfaces of coupling members 46, 48 are co-planar with bottom surface 56 of plate 42. Coupling members 46, 48 can be integrally formed with body portion 50, or attached thereto by welding, fasteners or other suitable attachment system.

Connecting elements 22, 24 are positionable in respective ones of the passages 82, 84 to couple stabilization system 34 to plating system 40. Connecting elements 22, 24 are axially movable in passages 82, 84 to adjust the relative positioning between the connecting elements 22, 24 and plate 42. Walls 78, 80 constrain the connecting element 22, 24 positioned thereon radially about the axis of the connecting element 22, 24 to facilitate bending of the connecting elements relative to plate 42 while permitting simultaneous axial adjustment of the connecting elements 22, 24 relative to plate 42. Connecting elements 22, 24 are radially constrained along the length of the portion of the connecting element positioned in the respective coupling member 46, 48. The length of coupling members 46, 48 provides a range of locations along coupling members 46, 48 to which the respective connecting element 22, 24 can be engaged for axial constraint thereof, permitting axial adjustment of the connecting elements relative to plate 42 without adjusting the position of plate 42 along the occiput.

Figures 13, 14:
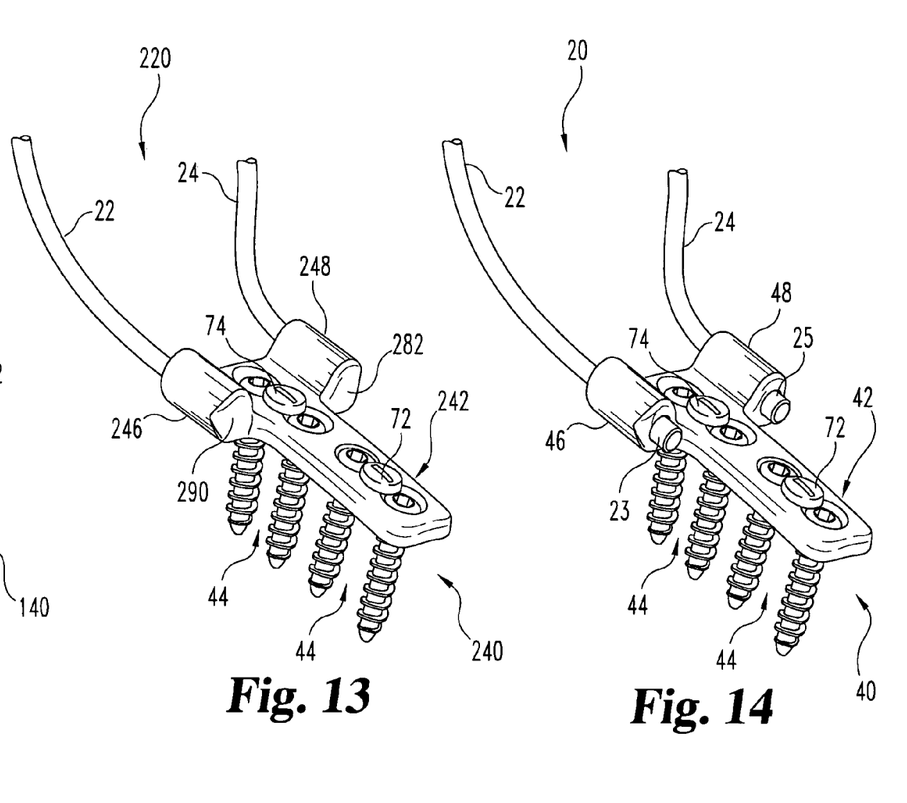
FIG. 13 is a perspective view of the midline occipital vertebral fixation system with the plate of FIG. 11.
FIG. 14 is a perspective view of the midline occipital vertebral fixation system with the plate of FIG. 3.

In FIG. 3, plate 42 includes coupling member 46 having passage 82 extending between and opening at the cephalad and caudal ends of coupling member 46. Similarly, passage 84 of coupling member 48 extends between and opens at the cephalad and caudal ends of coupling member 48. Passages 84, 86 can include a cross-section sized and shaped to telescopingly receive the cephalad end of connecting elements 22, 24 therein, as shown in FIG. 14.

In order to secure connecting elements 22, 24 in passages 84, 86, the cephalad ends 23, 25 of connecting elements 22, 24 are placed in the respective passages 84, 86 and axially adjusted relative the respective coupling member 46, 48 so that stabilization system 20 provides the desired fit with the patient anatomy. Since the cephalad ends 23, 25 are visible through the cephalad end openings of passages 84, 86, the location of connecting elements 22, 24 in coupling members 46, 48 can be verified. Coupling members 46, 48 can then be secured to connecting elements 22, 24. In one embodiment, it is contemplated that coupling members 46, 48 are crimped about respective ones of the connecting elements 22, 24. By providing internal engagement of the coupling members 46, 48 to connecting elements 22, 24, fasteners, clamps or other coupling mechanism external of coupling members 46, 48 can be eliminated, reducing potential sources of tissue irritation. In another embodiment, cephalad ends 23, 25 of connecting elements 22, 24 extend cephaladly from passages 84, 86 and ends 23, 25, and the ends 23, 25 are crimped to prevent their passage caudally into passages 84, 86.

It is contemplated that ends 23, 25 can be trimmed if necessary to minimize the cephalad extension of connecting elements 22, 24 from coupling members 46, 48. Other embodiments contemplate securing connecting elements 22, 24 to coupling members 46, 48 by welding, adhesives, set screws, or pins, for example. In the illustrated embodiment, passages 84, 86 and connecting elements 22, 24 each include a circular cross-section. Other embodiments contemplate non-circular cross-sections for passages 84, 86 and/or connecting elements 22, 24.

Figure 10:
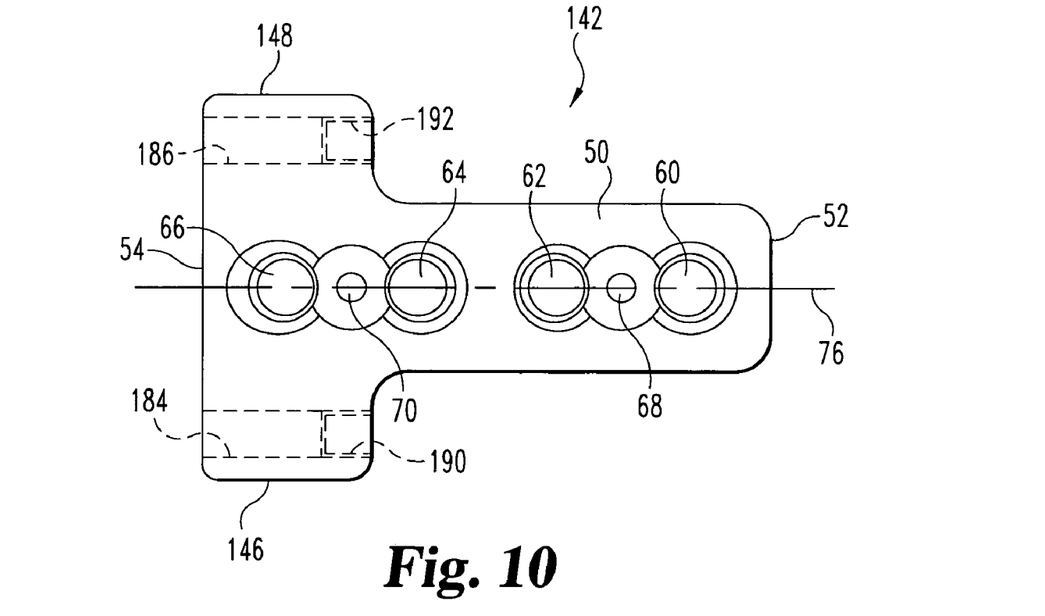
FIG. 10 is a plan view of another embodiment plate.
Figure 12:
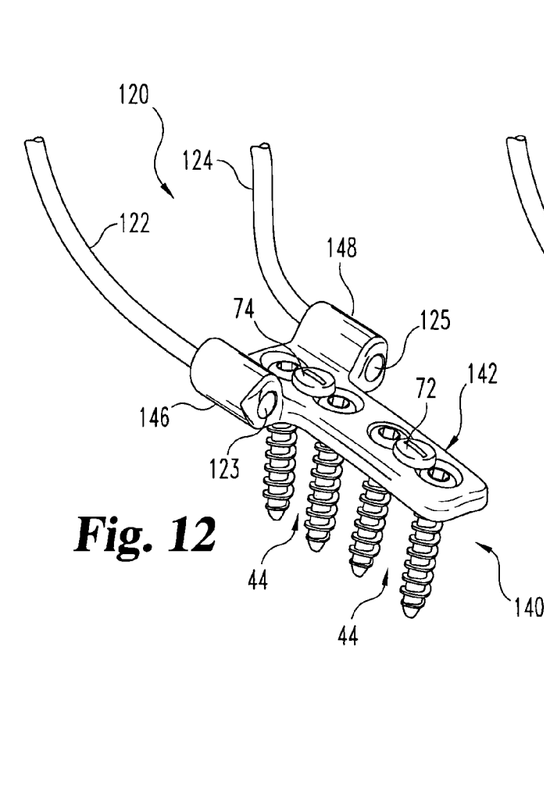
FIG. 12 is a perspective view of the midline occipital vertebral fixation system with the plate of FIG. 10.

In another embodiment shown in FIGS. 10 and 12, there is provided plating system 140 that includes a plate 142 substantially identical to plate 42 discussed above. Plate 142, however, includes coupling members 146, 148 with passages 184, 186, respectively, each of which include internal threaded portions 190, 192, respectively. Connecting elements 122, 124 can be substantially identical to connecting elements 22, 24 discussed above, but include cephalad ends 123, 125 that threadingly engage respective ones of the threaded portions 190, 192.

Threaded portions 190, 192 can be located at the cephalad end of the respective passage 184, 186 so that sliding axial adjustment of connecting elements 122, 124 can be provided at the caudal ends of passages 184, 186 with radial constraint. When engaged to threaded portions 190, 192, connecting elements 122, 124 are axially adjustable in coupling members 146, 148, but are constrained cephaladly and caudally upon engagement with threaded portions 190, 192. Further axial adjustment can be provided by threadingly moving the connecting elements relative to coupling members 146, 148. It is also contemplated that coupling members 146, 148 can be crimped to connecting elements 122, 124 to resist unthreading, and/or to engage connecting elements 122, 124 to coupling members 146, 148 in the unthreaded portions of passages 184, 186.

Figure 11:
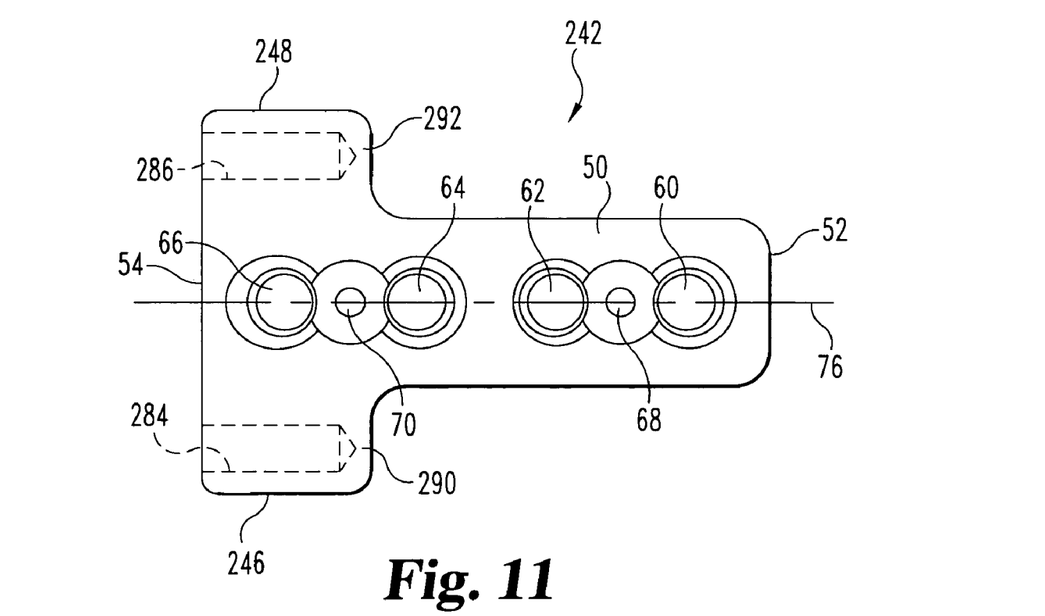
FIG. 11 is a plan view of another embodiment plate.

In another embodiment shown in FIGS. 11 and 13, there is provided plating system 240 that includes a plate 242 with coupling members 246, 248. Plating system 240 can be identical to plating system 40 discussed above, except that coupling members 246, 248 include end walls 290, 292 at the cephalad ends of passages 284, 286, respectively. The cephalad ends of connecting elements 22, 24 can abut end walls 290, 292 when fully seated in coupling members 246, 248. In this embodiment, connecting elements 22, 24 are radially constrained by coupling members 246, 248 and axially constrained in the cephalad direction when in abutting engagement with end walls 290, 292. It is contemplated that coupling members 246, 248 can be crimped to secure connecting elements 22, 24 thereto. It is further contemplated that set screws or other fasteners can be positioned through coupling members 246, 248 to secure connecting elements 22, 24 therein. Connecting elements 22, 24 can be provided with markings along the length thereof. Sight holes can also be provided in coupling members 246, 248. The markings and/or sight holes can allow the surgeon to obtain a visual indication of the depth of insertion of connecting elements 22, 24 in coupling members 246, 248.

Fastening systems for engagement of the plates to the occiput can include one or more bone screws 44 to secure plate 42 and one or more retaining systems to prevent the one or more bone screws from backing out of the plate when implanted. In the illustrated embodiment, there is provided a cephalad pair of bone screws 44 and a caudal pair of bone screws 44. Other bone engaging fasteners and/or systems for securing plate 42 to the occiput are also contemplated, such as staples, sutures, spikes, cables, and wires, for example. In one specific embodiment, bone screws 44 include a threaded shaft with a length sufficient to obtain bi-cortical purchase in the occiput.

Vertebral fixation system 34 further includes anchors 28 and 30 to fix or secure connecting elements 22, 24 to the vertebrae along which each extends. Anchors 28, 30 can be any type of anchor for securing connecting elements 22, 24 to the vertebrae. In the illustrated embodiment, anchors 28, 30 are multi-axial screws such as are provided with the Vertex™ System sold by Medtronic Sofamor Danek, Inc. and are engaged to the pedicles of the vertebrae. Other embodiments contemplate other forms for anchors 28, 30, including hooks, staples, uni-axial screws, cables, wires, sutures and combinations thereof, for example.

Figure 15:
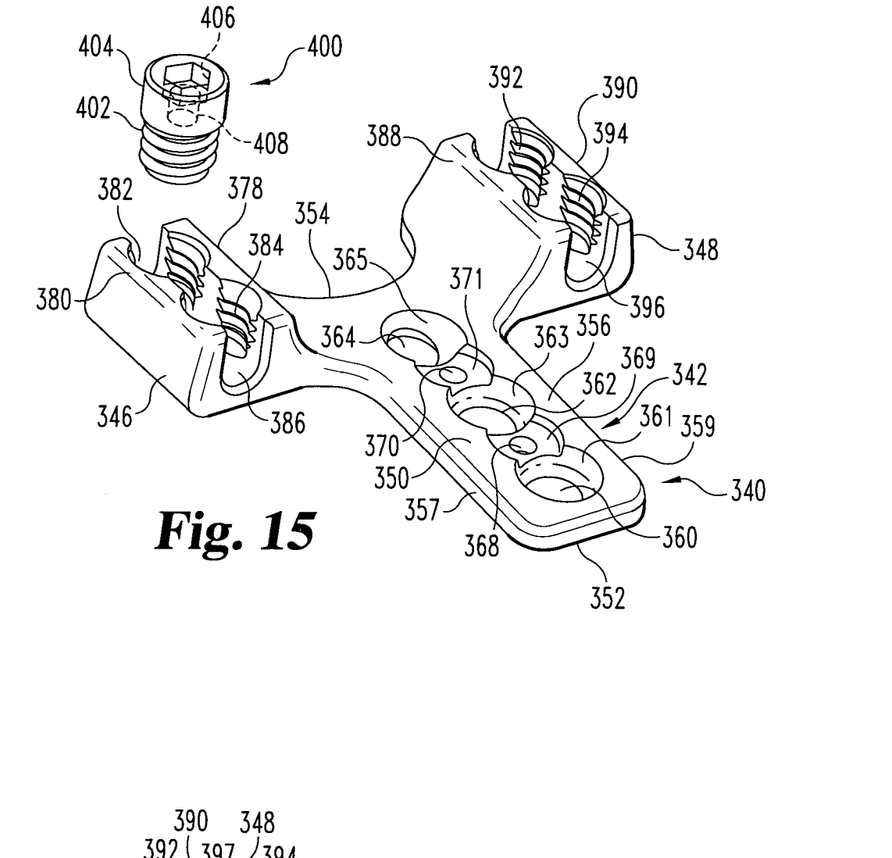
FIG. 15 is a perspective view of another embodiment plate.
Figure 16:
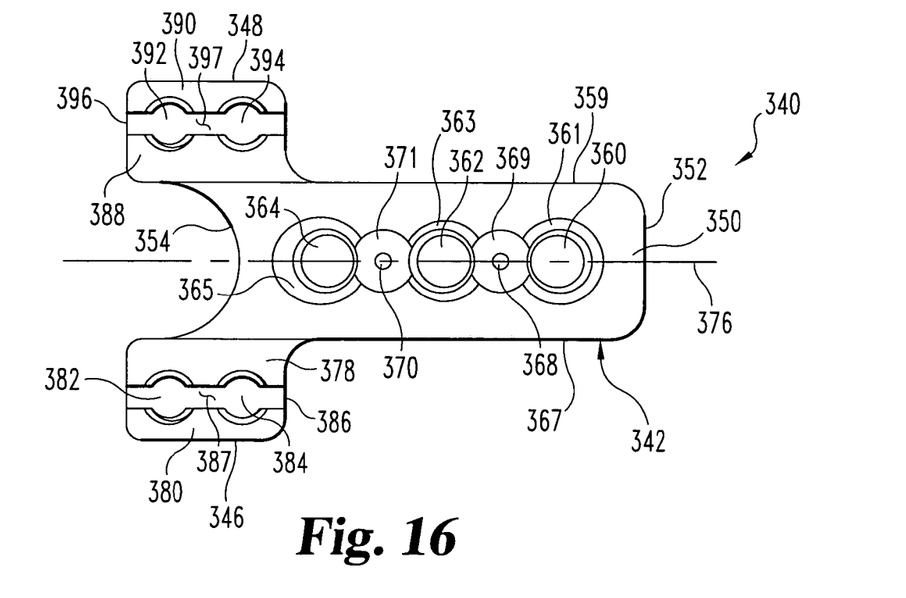
FIG. 16 is a plan view of the plate of FIG. 15.

Referring now to FIGS. 15-16, there is shown another embodiment plating system 340 that can comprise a portion of an occipital-vertebral fixation system that includes a vertebral fixation system, such as vertebral fixation system 34 discussed above. Plating system 340 can be secured to the occiput as discussed above with respect to plating system 40.

Plating system 340 includes plate 342 with a central body portion 350 extending between an upper or cephalad end 352 and a lower or caudal end 354. Body portion 350 includes a rectangular shape cephaladly of coupling members 346, 348. Body portion 350 includes a top surface 356, a bottom surface 358 and sidewalls 357, 359 extending therebetween. When implanted, bottom surface 358 is positioned along the occiput and top surface 356 is oriented away from the occiput. Plate 342 can include bottom surface 358 that is concavely curved along longitudinal axis 376 to conform to the profile of the base of the occiput along the medial nuchal line when positioned thereon. Top surface 356 can be convexly curved and parallel to bottom surface 358, although non-parallel configurations are contemplated.

Plate 342 includes a number of bores 360, 362, 364 that extend between and open at top surface 356 and bottom surface 358 for receiving bone engaging fasteners therethrough. First bore 360 includes a fastener bearing surface 361 adjacent top surface 356 having a spherical shape that contacts a correspondingly shaped spherical surface of the head of the bone engaging fastener positioned in bore 360. The complementary-shaped spherical surface allows the bone engaging fastener to assume any one of a plurality of angles relative to plate 342 about the center axis of bore 360. Second bore 362 includes a fastener bearing surface 363 adjacent to top surface 356 that is similar to fastener bearing surface 361, and third bore 364 also includes a fastener bearing surface 365 adjacent to top surface 356 that is similar to fastener bearing surface 361.

It is contemplated that bores 360, 362, 364 and the bone engaging fasteners therein can be configured so that the heads of the fasteners are recessed below top surface 356 when positioned in contact with bearing surfaces 361, 363, 365. This configuration minimizes the profile of plating system 340 extending from the occiput and the intrusion of the fastener heads into the surrounding tissue. Other embodiments contemplate that plate 342 is provided with less than three bone engaging fastener bores or more than three bone engaging fastener bores. The bone engaging fasteners and bores can also be adapted to provide a fixed orientation between the plate and the bone engaging fastener. Combination of fixed and variable angle engagement of the bone engaging fasteners for the same plate are also contemplated. In the illustrated embodiment, bores 360, 362, 364 are aligned along longitudinal axis 376 so that the width of plate 342 transversely to longitudinal axis 376 can be minimized. It is further contemplated that one or more of the bone engaging fastener bores can be offset to one side or the other of longitudinal axis 376, and also that bores can be positioned side-by-side on opposite sides of axis 376 to provide bi-lateral fixation.

A retaining system receptacle 368 is formed between and in communication with bores 360, 362. A first retaining system, such as discussed above with respect to retaining systems 72, 74, can be positioned in receptacle 368 to prevent back-out of bone engaging fasteners positioned in first and second bores 360, 362. A second retaining system receptacle 370 is formed between and in communication with bores 364, 366. A second retaining system can be positioned in receptacle 370 to prevent back-out of bone engaging fasteners positioned in first and second bores 364, 366.

Receptacle 368 includes a flared upper portion 369 in communication with bores 360, 362 so that a portion of the retaining system can contact or be positioned adjacent the heads of the bone engaging fasteners in bores 360, 362. Receptacle 370 includes a flared upper portion 371 in communication with bores 362, 364 so that at least a portion of the second retaining system can contact or be positioned adjacent the heads of the bone engaging fasteners in bores 362, 364.

Retaining systems embodiments other than retaining systems 72, 74 are also contemplated for plate 342. In addition, it is contemplated that plate 342 can be provided without any retaining system receptacles or retaining systems. In this embodiment, the bone engaging fasteners 44 positioned through bores 360, 362, 364 can be provided with a threaded shank having a length sufficient to obtain bi-cortical purchase in the occiput. Other types of bone engaging fasteners are also contemplated.

Plate 342 has a length extending along central longitudinal axis 376. First coupling member 346 projects laterally from central body portion 350 along one side of axis 376, and second coupling member 348 projects laterally from body portion 350 along the opposite side of axis 376. Coupling members 346, 348 can be elongated and extend generally parallel to axis 376 along at least a portion of the length of central body portion 350. In the illustrated embodiment, coupling members 346, 348 protrude caudally from lower end 354, and extend toward upper end 352 in the direction of longitudinal axis 376. Lower end 354 includes a concave curvature between coupling members 346, 348 to provide an anatomical fit with the base of the occiput, allowing coupling members 346, 348 to be positioned more caudally on the occiput and minimizing the length of the connecting elements between the cervical vertebrae and the occiput.

In one embodiment, it is contemplated that the length of each of the coupling members 346, 348 is about 5 percent or more of the length of plate 342. In another embodiment, the length of each of the coupling members 346, 348 ranges from about 5 percent to about 50 percent of the length of plate 342. In a further embodiment, it is contemplated that the length of each of the coupling members 346, 348 ranges from about 15 percent to about 35 percent of the length of plate 342. In yet another embodiment, the length of each of the coupling members 346, 348 is about 25 percent of the length of plate 342. The length of coupling members 346, 348 provides secure engagement of the connecting element positioned therein with plate 342.

Coupling members 346, 348 protrude laterally from respective ones of the lateral sidewalls 357, 359 of central body portion 350 away from longitudinal axis 376. Coupling members 346, 348 further include a height 386 such that each of the coupling members 346, 348 extends above top surface 356 of body portion 350. The bottom surfaces of coupling members 346, 348 lie in the same plane as the bottom surface of plate 342. Coupling members 346, 348 can be integrally formed with body portion 350, or attached thereto by welding, fasteners or other suitable attachment system.

Coupling member 346 includes lateral walls 378, 380 forming receptacles 382, 384 therebetween that open toward a top surface of coupling member 346. A longitudinal passage 386 extends between receptacles 382, 384 and opens at the cephalad and caudal ends of coupling member 346. Similarly, coupling member 348 includes lateral walls 388, 390 forming receptacles 392, 394 therebetween that open toward a top surface of coupling member 348. A longitudinal passage 396 extends between receptacles 392, 394 and opens at the cephalad and caudal ends of coupling member 348. Passages 386, 396 extend at least partially through coupling members 346, 348 and in a direction generally parallel to longitudinal axis 376.

Connecting elements 22, 24 are positionable in respective ones of the passages 386, 396 to couple vertebral fixation system 34 to plating system 340. Connecting elements 22, 24 are axially movable in passages 386, 396 to adjust the relative positioning between the connecting elements 22, 24 and plate 342. Walls 378, 380 and walls 388, 390 medially and laterally constrain connecting elements 22, 24 relative to longitudinal axis 376 to, for example, facilitate bending of the connecting elements relative to plate 342 while providing axial adjustment capabilities relative to plate 342. The length of coupling members 346, 348 provides a range of locations along coupling members 346, 348 to which the respective connecting element 22, 24 can be engaged. In the illustrated embodiment, connecting elements 22, 24 are at least constrained in the medial-lateral directions along the length of the portion of the connecting element positioned in the respective coupling member 346, 348. Radial constraint of connecting elements 22, 24 is provided with fastening members secured in receptacles 382, 384 and receptacles 392, 394.

In the illustrated embodiment, receptacles 382, 384, 392, 394 are internally threaded and adapted to receive an externally threaded fastening member. The fastening members can be, for example, in the form of set screws, such as set screw 400. The fastening members can contact the connecting elements 22, 24 in the respective passage 386, 396 to clamp the connecting elements 22, 24 between the fastening member and the bottom surface 387, 397 along the respective passage 386, 396. The fastening members can be provided with penetrating elements and/or surface features that provide frictional engagement with the connecting element 22, 24 when in contact therewith.

In the illustrated embodiment, set screw 400 includes a distal threaded portion 402 and a proximal break-off portion 404. Proximal portion 404 includes an internal tool engaging recess 406 to facilitate engagement with a driving tool. Proximal portion 404 can break-off or sever from distal portion 402 when the desired amount of torque has been applied to the connecting element 22, 24 by engagement with the distal end of set screw 400. After break-off of proximal portion 404, distal portion 402 remains in the respective receptacle and can be recessed at or below the top surface of the coupling member 346, 348. Distal portion 402 can include a tool engaging recess 408 to receive a tool to further tighten or remove distal portion 402 when proximal portion 404 is severed.

Plate 342 includes coupling member 346 having passage 386 extending between and opening at the cephalad and caudal ends of coupling member 346. Similarly, passage 396 of coupling member 348 extends between and opens at the cephalad and caudal ends of coupling member 348. Passages 386, 396 can include a cross-section sized and shaped to receive the cephalad end of connecting elements 22, 24 therein while permitting axial adjustment of the connecting elements in passages 386, 396. The inner surfaces of walls 378, 380 and the inner surfaces of walls 388, 390 can contact the sides of the respective connecting element 22, 24 positioned therein to provide medial and lateral constraint of the connecting element while permitting axial adjustment of the connecting elements 22, 24 along passages 386, 396.

In order to secure connecting elements 22, 24 in passages 386, 396, the cephalad ends 23, 25 of connecting elements 22, 24 are placed in the respective passages 386, 396 and axially adjusted relative the respective coupling member 346, 348 so that stabilization system 20 provides a desired fit with the patient anatomy. Connecting elements 22, 24 can then be secured to coupling members 346, 348 with one or more fastening members in the coupling member receptacles 382, 384, 392, 394. Fastening members can be provisionally positioned in one or more of the receptacles 382, 384, 392, 394 prior to axial adjustment and/or bending of connecting elements 22, 24 to facilitate securement of connecting elements 22, 24 in the desired position. It is contemplated that ends 23, 25 can be trimmed if necessary to minimize or eliminate any cephalad extension of connecting elements 22, 24 from coupling members 346, 348.

One technique for implanting the system will be described with reference to system 20, it being understood that the technique can also be applied with the other embodiment systems discussed herein. Plate 42 can be contoured to lie along the occiput. Plate 42 can be placed along the median nuchal line of the occiput so that coupling members 46, 48 may lie either along or lateral to the median nuchal line. Connecting elements 22, 24 can be factory positioned and engaged in coupling members 46, 48 or positioned therein by the surgeon during surgery and crimped when the desired fit for system 20 has been obtained. Connecting elements 22, 24 can be provided in straight or pre-bent configurations. Connecting elements 22, 24 can be pre-contoured to fit the patient's anatomy, or contoured during surgery to provide a desired custom fit with the patient.

Connecting elements 22, 24 can be crimped to coupling members either in the factory or during surgery. The crimper used in surgery may be of a handheld or table top design. A table top design allows the connecting elements to be bent in situ and reduces fiddle factor in keeping the connecting elements in the desired alignment while crimping. An aluminum, nitinol or otherwise flexible template of the occiput vertebral fixation system may be supplied to the surgeon to aid the surgeon in custom contouring the connecting elements and/or the plate during surgery.

The plating systems are provided with occipital plates that include a low profile both extending from the occiput and laterally relative to the occiput. The plates can conform with the occipital fossas present between the foramen magnum and the superior nuchal line. The plating systems also allow the connecting elements to be axially adjusted relative to the plate to provide the desired fit with the patient anatomy while at least laterally constraining the connecting element to facilitate bending or contouring of the connecting elements. The plating systems also provide plates with bores for receiving bone engaging fasteners aligned along the median nuchal line, facilitating engagement of the plate in the area of the occiput with thick bone, and therefore, greater bone purchase. Bi-cortical placement of the bone engaging fasteners can also be eliminated, but is not precluded. The musculature covering this area of the occiput is dense, providing greater patient comfort with neck palpation. The systems do not require perforation of the occiput, decreasing the time and complexity of the surgical procedure.

Figure 17:
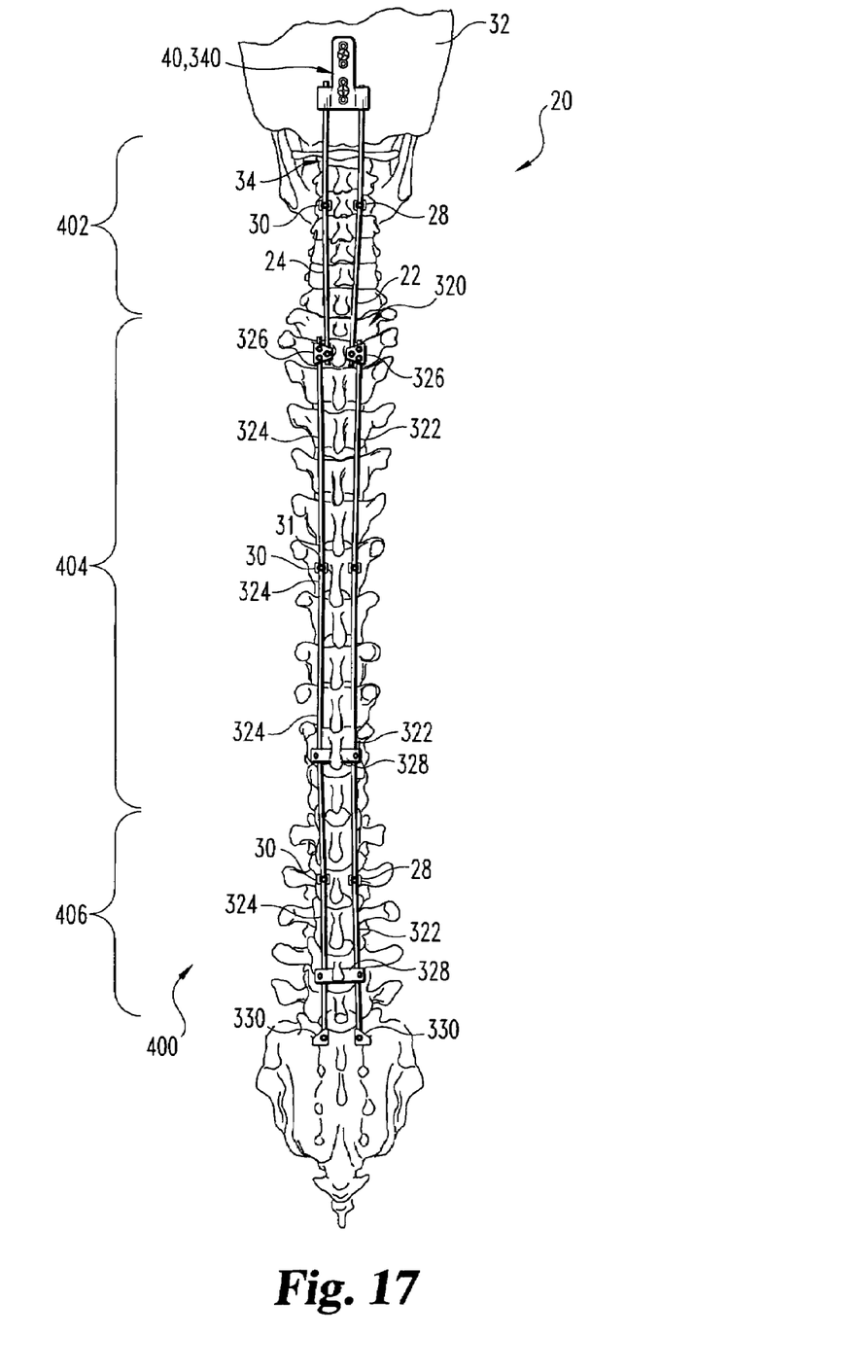
FIG. 17 is a diagrammatic illustration of the posterior side of the spinal column with a fixation system.

The occipital fixation systems discussed herein can also be employed with vertebral fixation systems that extend along the spinal column 400, such as caudal vertebral fixation system 320 shown in FIG. 17 in combination with occipital vertebral fixation system 20. For example, occipital vertebral fixation system 20 includes a plating system 40 or 340 engaged to occiput 32, and cervical vertebral fixation system 34 engaged to the cervical region 402 of spinal column 400. Connecting elements 22, 24 of occipital vertebral fixation system 20 extend caudally to offset connectors 326 positioned adjacent the transition from cervical region 402 to thoracic region 404. Connecting elements 22, 24 are engaged to respective ones of the offset connectors 326. Offset connectors 326 are further coupled to caudal connecting elements 322, 324. Caudal connecting elements 322, 324 extend caudally therefrom along thoracic region 404 and lumbar region 406. Sacral couplers 330 engage the caudal ends of caudal connecting elements 322, 324 to sacral region 408.

Caudal vertebral fixation system 320 includes offset connectors 326 to couple connecting element 22, 322 and connecting elements 24, 324 to one another and to provide a continuous fixation system along spinal column 400. Connecting elements 22, 24 can each have a cross-section that is smaller than the cross-section of connecting elements 322, 324, facilitating placement of connecting elements 22, 24 along the cervical regions, and placement of the larger connecting elements 322, 324 along the larger thoracic and lumbar regions. A number of transverse connectors 328 can further be provided that extend transversely to the central axis of the spinal column between the adjacent connecting elements 322, 324 or adjacent connecting elements 22, 24. Transverse connectors 328 engage the adjacent connecting elements to facilitate maintain the alignment of the connecting elements along the spinal column. Anchors 28, 30, as discussed above, can be multi-axial screws with set screws 32 engaging the connecting elements 22, 24, 322, 324 to the pedicles of spinal column 400.

Figure 18:
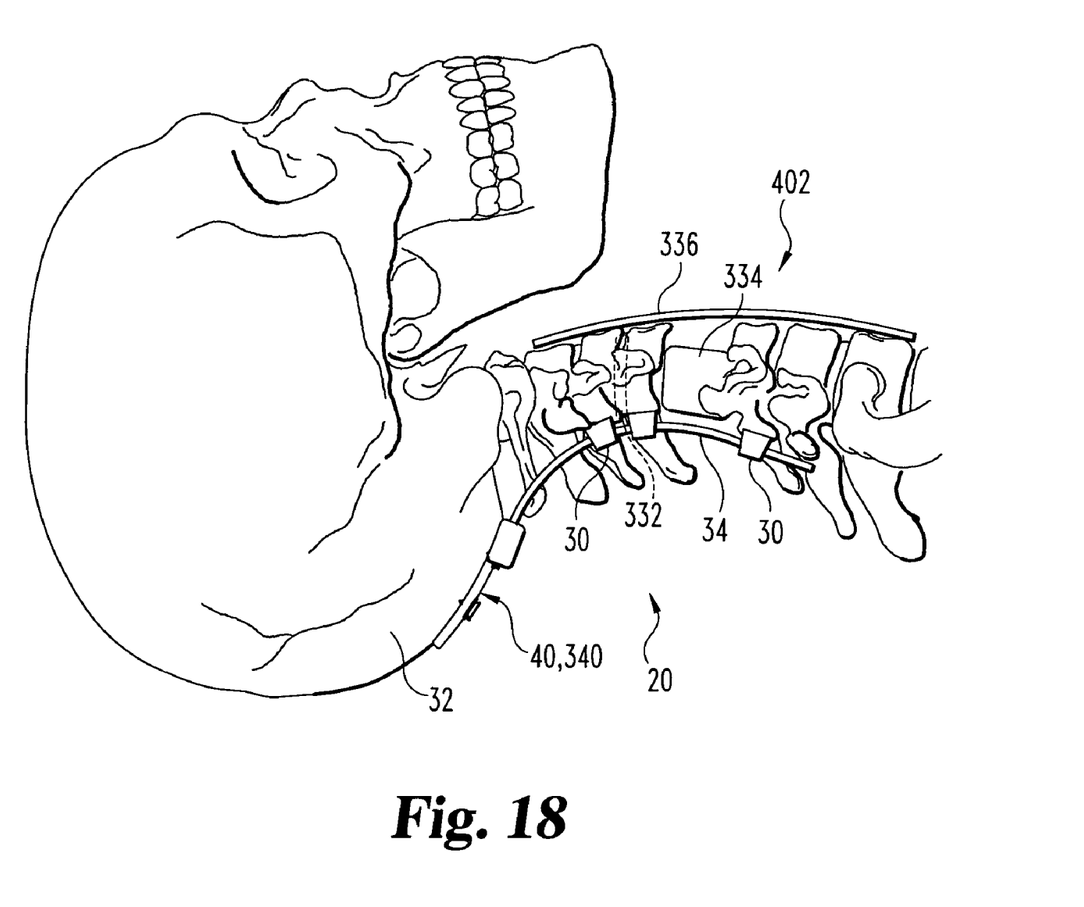
FIG. 18 is a diagrammatic illustration looking laterally at the cervical portion of the spinal column with a fixation and implant system.

Referring to FIG. 18, there is shown a lateral view of the occiput and cervical vertebrae 402. Occiput vertebral fixation system 20 is secured along the occiput and the posterior side of cervical region 402. Implants can be position between vertebrae of cervical region 402, such as implant 332 in the disc space, or implant 334 positioned to replace one or more removed vertebrae in a corpectomy procedure. Anterior stabilization can be provided with anterior plating system 336 secured along one or more vertebral levels of cervical region 402.

According to one aspect, an occipital plating system includes a plate having at least one coupling member laterally positioned relative to a longitudinal axis of the plate and extending longitudinally along a portion of the plate.

According to a further aspect, an occipital plating system includes a plate having at least one coupling member laterally offset from and extending in the direction of a longitudinal axis of the plate. In one embodiment, the at least one coupling member includes a pair of coupling members protruding laterally from and extending along a portion of the length of a central plate portion along opposite sides thereof.

According to another aspect, an occipital plating system includes a plate having at least one coupling member extending longitudinally along the plate configured to receive an elongated connecting element, such as a rod. The connecting element extends along an axis and is simultaneously axially adjustable and radially constrained by the coupling member when positioned therein.

In one embodiment, the coupling member includes a first portion that allows axial adjustment of the connecting element and a second portion that axially constrains the connecting element when the connecting element is in engaged with the second portion. In one form, the second portion of the coupling member constrains the connecting element cephaladly when the connecting element is engaged therewith. In another form, the second portion of the coupling member constrains the connecting element cephaladly and caudally when the connecting element is engaged therewith.

According to another aspect, an occipital plating system includes a plate having at least one coupling member. The at least one coupling member is internally engageable to the connecting element without employing an external fastening system to secure the coupling member to the connecting element.

According to another aspect, an occipital plating system includes a plate having at least one coupling member. The at least one coupling member includes a passage having a length adapted to radially constrain a connecting element positioned therein.

According to another aspect, an occipital plating system includes a plate having at least one coupling member extending longitudinally along the plate configured to receive an elongated connecting element, such as a rod. The connecting element extends along an axis and is simultaneously axially adjustable and laterally constrained by the coupling member when positioned therein. One or more fixation fasteners are engageable with the coupling member to axially and radially secure the connecting element in the coupling member.

According to another aspect, an occipital plating system includes a plate having at least one coupling member laterally offset from and extending longitudinally along a central plate portion. The coupling member is configured to receive an elongated connecting element, such as a rod. The connecting element extends along an axis and is simultaneously axially adjustable and laterally constrained by the coupling member when positioned therein. One or more fixation fasteners are top-loaded for engagement with the coupling member to secure the connecting element therein.

According to another aspect, an occipital plating system includes a plate having a concavely curved caudally oriented end surface when secured to the occiput.

According to another aspect, an occipital plating system includes a plate having a concavely curved caudally oriented end surface extending between a pair of coupling members laterally offset from and extending longitudinally along a central plate portion.

According to another aspect, an occipital plating system includes a plate having at least one coupling member laterally offset from and extending longitudinally along a central plate portion. The at least one coupling member is configured to receive an elongated connecting element, such as a rod. The coupling member includes a first fastener receptacle and a second fastener receptacle spaced longitudinally therealong to receive fixation fasteners to secure the connecting element therein.

According to another aspect, an occipital plating system includes a plate having at least one coupling member extending longitudinally along the plate configured to receive an elongated connecting element, such as a rod. The coupling member includes a first fastener receptacle and a second fastener receptacle spaced longitudinally therealong to receive fixation fasteners to secure the connecting element therein.

While the invention has been illustrated and described in detail in the drawings and foregoing description, the same is to be considered as illustrative and not restrictive in character. All changes and modifications that come within the spirit of the invention are desired to be protected.

What is claimed is:

1. An occipital plating system, comprising:
a plate extending along a longitudinal axis and including a bottom surface profile adapted for positioning along the medial nuchal line of the occiput and an opposite top surface, said plate including a length along the longitudinal axis between a cephalad end and a caudal end;
at least one coupling member extending from said plate and offset laterally of the longitudinal axis of said plate, said at least one coupling member including a bottom wall and a pair of lateral walls extending from said bottom wall and along opposite sides of an elongated passage extending along a portion of said length of said plate to receive a cephalad end of an elongated connecting element in said passage, said pair of lateral walls defining a top surface of said coupling member opposite said bottom wall and said passage opens along said top surface of said coupling member between said lateral walls, said coupling member further including at least two receptacles along said passage with said pair of lateral walls each extending from said bottom wall to said top surface of said coupling member from one receptacle of said two receptacles to the other receptacle of said two receptacles of said coupling member, said at least two receptacles opening at said top surface of said coupling member in communication with said passage wherein said at least one coupling member forms a lateral extension of said plate along an adjacent lateral side of said plate, said at least one coupling member further extending caudally along said longitudinal axis from said daudal end of said plate; and
a pair of fasteners engaged in respective ones of said at least two receptacles in contact with said cephalad end of said connecting element to secure said cephalad end of said connecting element between said pair of fasteners and said coupling member.

2. The plating system of claim 1, wherein said elongated connecting element is axially adjustable in said passage of said coupling member prior to securement with said fastener.

3. The plating system of claim 1, wherein said pair of fasteners and said coupling member radially constrain said elongated connecting element in said passage.

4. The plating system of claim 1, wherein said pair of fasteners are each a set screw with a threaded distal portion, and said at least two receptacles are internally threaded for engagement with said threaded distal portion.

5. The plating system of claim 4, wherein said set screw includes a proximal portion severable from said distal portion upon application of a predetermined threshold torque thereto.

6. The plating system of claim 1, further comprising:
an implant positionable between cervical vertebrae of the spinal column.

7. The plating system of claim 6, further comprising:
a plate engageable along an anterior side of cervical vertebrae of the spinal column.

8. The plating system of claim 1, further comprising a fixation system positionable along a posterior side of the spinal column from cervical vertebrae to the sacral region.

9. The plating system of claim 8, wherein said fixation system includes multi-axial screws.

10. The plating system of claim 8, wherein said fixation system includes a transverse connector adapted to extend across the spinal mid-line and interconnect a pair of elongated connecting elements extending along the posterior side of the spinal column.

11. The plating system of claim 8, wherein said fixation system includes an offset connector adapted to axially couple a caudal end of said elongated connecting element and a cephalad end of a caudally extending elongated connecting element.

12. The plating system of claim 8, wherein said fixation system includes a sacral plate.

13. The plating system of claim 8, wherein said fixation system includes a pair of elongated caudal connecting elements positionable along respective sides of the spinous processes of the thoracic and lumbar vertebrae of the spinal column.

14. The plating system of claim 1, wherein said elongated connecting element includes a pair of elongated connecting elements positionable along respective sides of the spinous processes of the cervical vertebrae, said plate including a second coupling member opposite said at least one coupling member adapted to received a cephalad end of the other of said pair of elongated connecting elements.

15. The plating system of claim 1, wherein said at least two receptacles are each internally threaded.

16. The plating system of claim 15, wherein said at least one coupling member includes a second coupling member extending from said plate opposite said at least one coupling member, said second coupling member forming a second passage extending along a portion of said length of said plate to receive a cephalad end of a second elongated connecting element in said second passage, said second passage opening along a top surface of said second coupling member, said second coupling member further including a pair of receptacles opening along said top surface thereof and in communication: with said second passage for receiving fasteners spaced longitudinally along said second coupling member.

17. The plating system of claim 1, wherein said pair of lateral walls are spaced to contact sides of the connecting element in the passage to medially and laterally constrain the connecting element in the passage while permitting the connecting element to be moved along the passage.

* * * * *